United States Patent [19]
Kennedy

[11] Patent Number: 5,664,042
[45] Date of Patent: Sep. 2, 1997

[54] UNIVERSAL CHUCK

[76] Inventor: John Kennedy, 6 Serena La., R.R. #3, Guelph, Ontario, Canada

[21] Appl. No.: 433,850

[22] Filed: May 2, 1995

[51] Int. Cl.⁶ .................................................. G02B 6/14
[52] U.S. Cl. ............................ 385/136; 385/137; 385/134; 385/78
[58] Field of Search .................... 385/136, 137, 385/134, 76, 78, 81; 279/102

[56] References Cited

U.S. PATENT DOCUMENTS

| | | | |
|---|---|---|---|
| 4,317,615 | 3/1982 | Herold | 385/134 |
| 4,404,874 | 9/1983 | Lieser | 279/102 |
| 4,948,215 | 8/1990 | Friedman | 385/134 |

FOREIGN PATENT DOCUMENTS

| | | | |
|---|---|---|---|
| 1-32210 | 2/1989 | Japan | 385/78 |

*Primary Examiner*—Rodney B. Bovernick
*Assistant Examiner*—Yisun Song
*Attorney, Agent, or Firm*—Bereskin & Parr

[57] ABSTRACT

A chuck is provided to hold a fibre optic light guide of the type typically used in medical dental procedures involving the curing of resins by exposure to light. The chuck has an internal bore and configuration to releasably support and retain a fibre optic light guide so that fibre optic light guides may be readily substituted between patients. The chuck thus facilitates sterilization/disinfection procedures. The outside diameter and configuration of the chuck is adapted to fit a particularly manufacturer's curing light device to adapt a particular manufacturer's instrument for use with the replaceable fibre optic light guides. A set of chucks may be manufactured with the outside diameter of the chucks adapted to be received in a number of different manufacturers' light emitting devices but all such chucks have a common internal diameter so that the replaceable fibre optic light guides may be used with any of the plurality of manufacturers' instruments.

10 Claims, 4 Drawing Sheets

UNIVERSAL CHUCK

FIELD OF THE INVENTION

This invention relates broadly to light emitting apparatus for curing photocurable materials used in human medical applications, in particular, the invention relates to fibre optic light guides to be used in conjunction with treatments of human beings.

Certain materials which are used medically in the treatment of human beings are cured upon exposure to a source of light. Materials of the type in question may be used as adhesives, sealants or restorative materials. In other cases the light activated material may be used to deliver drugs utilizing patches mounted on the skin of the patient, which patches are exposed from time to time to appropriate doses of light energy.

It is particularly common to make use of light curable materials in the field of dentistry. Dental materials may be used particularly as restorative materials when working on teeth. These materials are applied by the dentist to the patient and then when positioned are exposed to a suitable light energy and cured in place.

Typically the light energy of appropriate wavelength and power may be generated by some type of light emitting device. The device may be in the form of a gun having a handle to be used by the medical professional and a body in which the light generating source is located. Devices of this type may be either fully portable, that is, powered by batteries or may be attached to supply lines. The supply lines as well as providing electrical energy may provide cooling in the form of air or other fluids as appropriate.

Examples of gun type devices used in the dental field are illustrated in U.S. Pat. No. 5,147,204 issued to Minnesota Mining and Manufacturing Co. and dated Sep. 15, 1992. Devices of the type in question are available from such suppliers as L. D. Caulk, division of Dentsply International, Demetron Research Corporation and Minnesota Mining and Manufacturing Co., among others.

Almost all such devices in common have some type of fibre optic guide which transmits the light from the light source to a work site. The fibre optic guide may be of convenient length and configuration and is often supplied with some form of curved end to assist in directing the light to a specific spot which may then be manoeuvred by the medical professional to the desired location. Examples of patents which discuss the nature of the fibre optic light guides are U.S. Pat. No. 4,846,546 issued to Joseph Cuda dated Jul. 11, 1989, U.S. Pat. No. 5,290,169 issued to Joshua Friedman dated Mar. 1, 1994 and U.S. Pat. No. 5,312,249 issued to John Kennedy and dated May 17, 1994.

As is commonly understood when medical instruments are used for the treatment of human beings, appropriate cleanliness is required. The term sterilization is most typically used to denote the use of either physical or chemical agents to eliminate all viable microbes from a material, while the term disinfection generally refers to the use of germicidal chemical agents to destroy potential infectivity of a material. The term sanitizing refers to procedures used to lower the bacterial content of utensils but without necessarily sterilizing such utensils. Disinfectants of course must be effective against all kinds of microbes. Throughout this description the term disinfection or disinfect will be used more broadly to encompass sterilization and sanitizing.

Disinfection of fibre optic light guides is required when treating patients. The need to disinfect fibre optic light guides for dental procedures has been discussed and is well recognized. One example is the article entitled Disinfection of Visible Light Curing Devices which appeared in the journal Operative Dentistry Winter 1989, volume 14, number 1 published by Operative Dentistry Inc., Seattle, Wash., U.S.A.

Fibre optic light guides vary considerably in their expense. Fibre optic light guides with certain construction are relatively expensive. The expense of such fibre optic light guides means that they must be reusable. If the guide is to be reused then it must be subject to being disinfected before reuse with another patient. On the other hand other types of fibre optic guides are relatively inexpensive and in certain circumstances may be suitable for single use applications. Single use fibre optic light guides typically are disinfected at the original point of manufacture and distributed in clean packages so that the dental professional may be assured that a disinfected fibre optic is available upon commencement of a procedure with a patient.

One of the problems with existing devices is the suitability and ease with which the fibre optic light guide may be removed and substituted in the housing containing the light emitting device. There is also the question of the cost of the fibre optic light guides and the attendant expense of having a sufficient supply on hand for the medical professional to carry on a practice while still at the same time disinfecting those fibre optic light guides not in use for subsequent use on different patients. Accordingly, there is a need to devise a system that would permit ready substitution of fibre optic light guides for use in association with existing light emitting devices.

In accordance with the present invention there is provided a chuck for use with a medical instrument having a light emitting device in which light is delivered through a fibre optic delivery means to a work site. The chuck comprises a housing which has an external configuration which is adapted to be received within the desired medical instrument which has light emitting means. The housing defines a central bore extending through the housing. The central bore is sized to receive a fibre optic light guide. The housing is configured to align a fibre optic light guide received within the bore with the light emitting means so that light from the light emitting means passes into the fibre optic light guide. The bore releasably supports and retains the fibre optic light guide so that a first fibre optic light guide may be removed from the bore and replaced by a disinfected second fibre optic light guide.

Further, in accordance with the present invention a set of 2 or more universal chucks is provided. The set of chucks is intended for use with a set of two or more medical devices each having a light emitting device and a fibre optic light guide. Each of the set of medical devices may have a different internal configuration for releasably retaining a fibre optic light guide. Each member of the set of universal chucks has an outside configuration corresponding to the internal configuration of a respective one of the set of medical devices. All of the universal chucks have a common internal configuration adapted to releasably retain a fibre optic light guide sized to fit the universal chuck in any of the medical devices.

BRIEF DESCRIPTION OF THE DRAWINGS

For a better understanding of the present invention, and to show more clearly how it may be carried into effect, reference will now be made, by way of example, to preferred embodiments of the present invention shown in the accompanying drawings, in which.

DETAILED DESCRIPTION OF THE PREFERRED EMBODIMENTS

Figure 1:
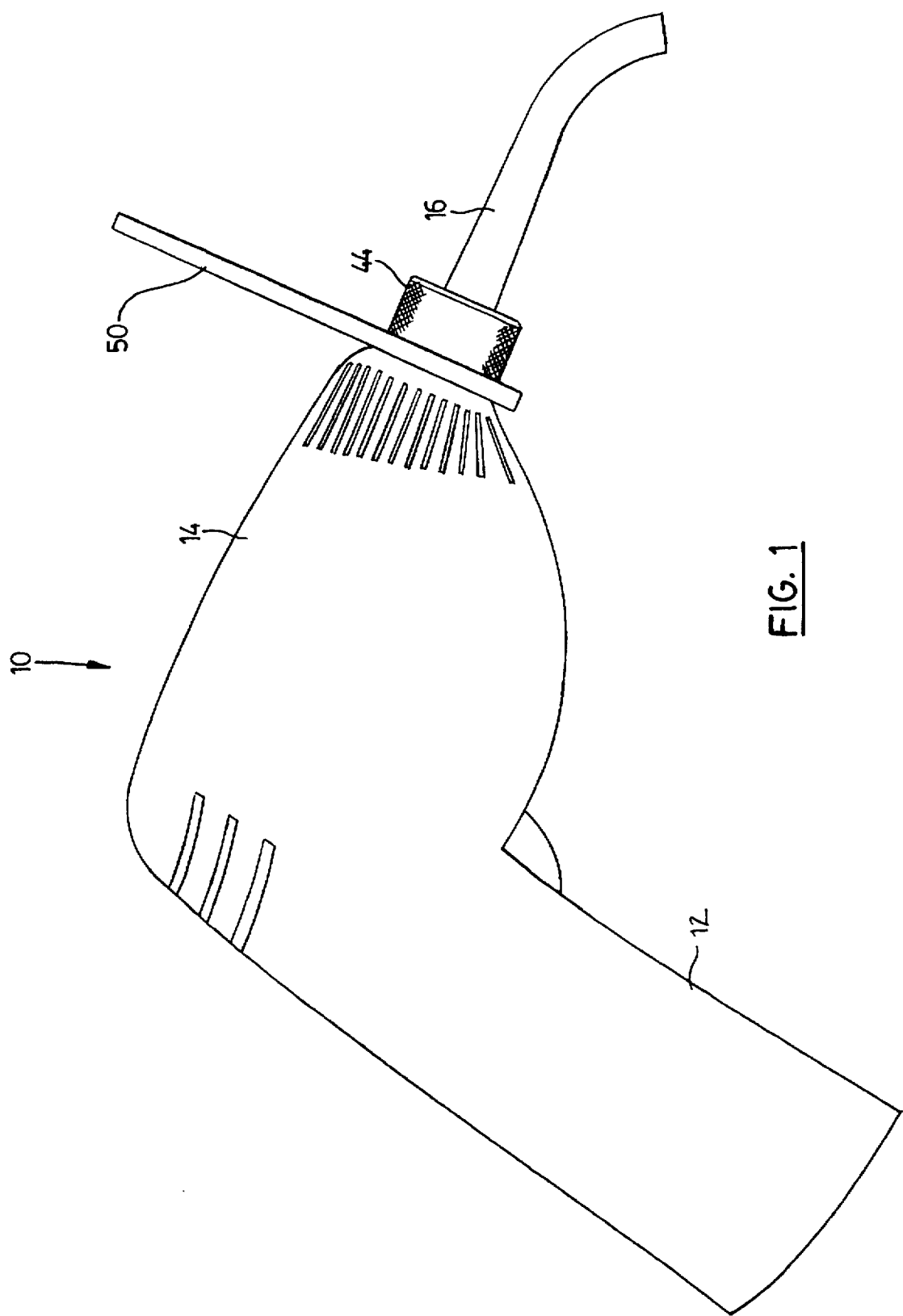
FIG. 1 shows in diagrammatic form a hand-held light emitting medical device in association with which the chuck of the present invention may be used.

Reference is first made to FIG. 1 which shows a hand held light emitting device in association with which the present invention is to be used. The device is in the form or a basic gun shape and is illustrated generally at 10. The gun 10 includes a handle portion 12 and a housing portion 14. A fibre optic light guide illustrated generally at 16 projects from the housing.

The housing 14 of the device 10 will contain a light emitting device such as a light bulb, laser or the like. The housing 14 will also contain an appropriate control mechanism for controlling the powering and timing of the light. The handle portion 12 is to be gripped by the medical professional in use. If the device 10 is battery powered the handle portion 12 is a convenient place for the location of the batteries. Where the device 10 is not battery powered then power supplies may conveniently be attached to the handle. Additionally, there may be other connections to the handle such as a source of cooling air if required or other cooling fluids and the like.

The fibre optic light guide 16 may be one of several different types. Optical fibres may be made of plastic, glass or silica. Plastic fibres while being the least efficient tend to be cheaper and more rugged. Although this is desirable in some uses this is not as important in the medical field where the light is conducted to a work site for use in curing or other photo initiated reactions.

A basic optical fibre consists of two concentric layers, the inner core and the outer cladding. The outer cladding has a refractive index smaller than that of the core. The characteristics of light propagation depend primarily on the fibre size, its construction, the refractive index profile and the nature of the particular light source.

Typically in the dental field or for other similar medical uses, fibre optical light guides may be made from plastic or glass. The cladding which is required for the structure to act as a light guide is different for glass and plastic. Typically a glass fibre optic light guide must be sheathed with a cladding layer. The cladding layer may be glass having a suitably different refractive index which sheaths the rod. Typically in the manufacture of glass fibre optics an end fitting is provided at the probe's light receiving end and may also be provided at the outlet end. Fibre optic light guides of this type are relatively expensive to manufacture not only because of the glass but also because of the end fittings which are required. Fibre optic light guides of this type for cost reasons normally must be capable of being disinfected so that they may be reused from patient to patient. The end fitting on a rod will be used to fit in the housing or chuck of the gun type light source for the particular manufacturer.

An alternative form of fibre optic light guide can be manufactured from relatively inexpensive plastic. Plastic fibre optic light guides have the unusual property that the air surrounding the plastic acts as a cladding layer. In such cases the plastic acts as a fibre optic light guide while surrounded by air. If on the other hand the plastic is contacted by a solid then there is an improper relationship between the index of refraction within the plastic and the index of refraction immediately next to the plastic and the plastic material will cease to function efficiently as a light guide.

Fibre optic light guides manufactured from plastic are relatively inexpensive. Because of the relatively inexpensive nature it is possible to consider such guides as single use light guides. When the intended purpose is single use then the light guide can be disinfected prior to packaging and then shipped to the dental office in a suitably sealed package. Where for economics, recycling or other reasons, it is preferred to disinfect the less expensive light guides then light guides that have been used are to be removed from the gun and suitably disinfected. The light guide may be disinfected by autoclaving or any other of the typical procedures to disinfect medical instruments.

Figure 4:
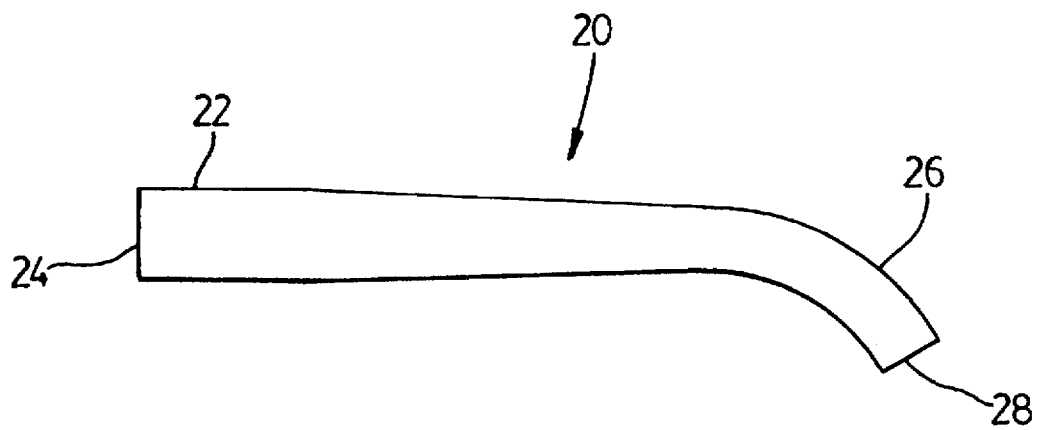
FIG. 4 is a side view of a fibre optic light guide to be used in association with the chuck illustrated in FIGS. 2 and 3.

As shown in FIG. 4 the typical light guide 20 will have a substantially cylindrical portion 22 at the light receiving end 24. The cylindrical portion is to be received within the housing of a light emitting apparatus 10 and aligned with the light so that the light emitted impinges on the receiving end 24 of the guide.

Typically the light guide 20 will be bent 26 at the end 28 remote from the gun 10. The angled bend 26 is to facilitate the directing of the light to the desired work site. Particularly in the case of use in curing of dental resins the light is used to cure resins which have been placed on the teeth. In order to efficiently direct the light squarely unto a tooth under reconstruction, a convenient bend is placed on the end of the tube so that the gun may be held in front of the patients head while directing all of the light onto a tooth as desired.

Figure 2A:
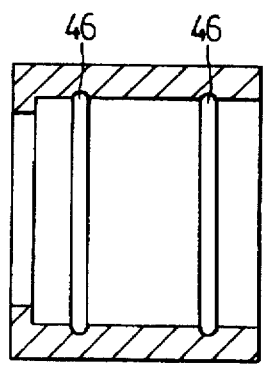
FIG. 2 is a side view through a chuck in accordance with the invention.
Figure 2:
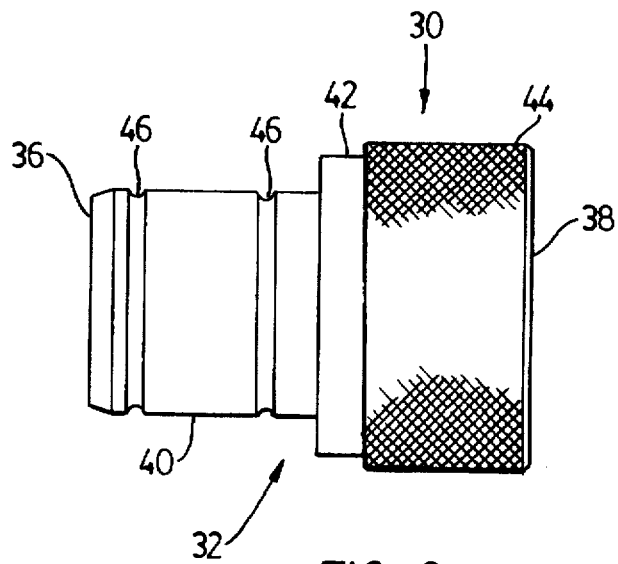
Figure 2C:
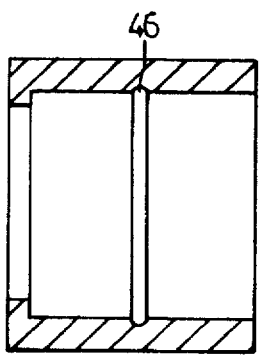
Figure 2B:
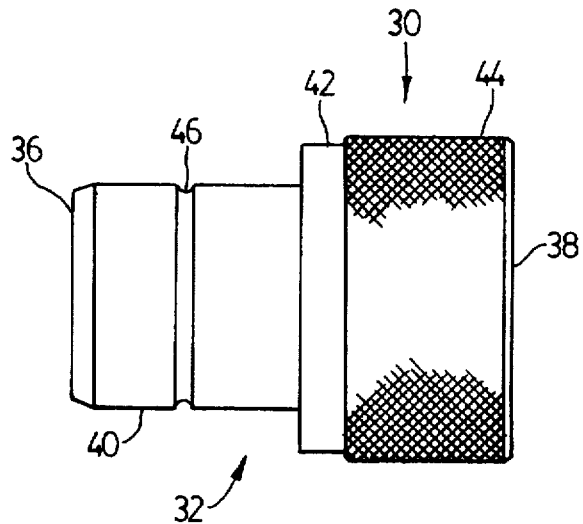
Figure 3:
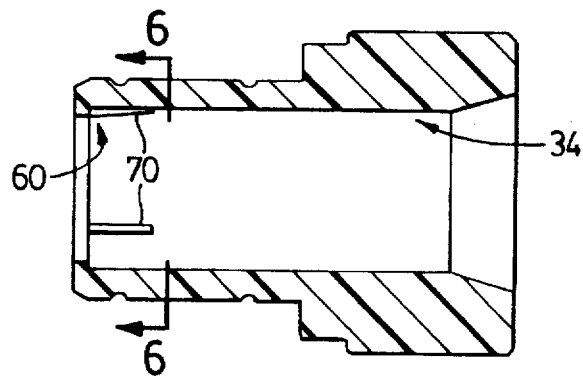
FIG. 3 is an sectional view of the chuck of FIG. 2.

Referring now to FIGS. 2 and 3, there is illustrated a chuck 30 for use with a gun type light emitting source. The chuck 30 comprises a housing 32. The housing 32 defines an internal bore 34 extending through the housing from one end 36 to the other 38. The housing 32 is configured on its external surface to provide a shank portion 40, a shoulder portion 42 and a grasping portion 44.

The shank portion 40 has a length and diameter adapted to be received within the existing permanently mounted chuck of the light emitting apparatus 10. Typically the permanently mounted chuck will be sized to receive the end fitting of a typical glass fibre optic light guide. As shown in FIG. 2 the external surface of the shank portion 40 may have one or more semi-circular grooves 46 for locating rubber O-rings or the like. The rubber O-rings may be installed in the grooves 46 on the shank 40 and serve to form a snug fit between the chuck permanently attached to the light emitting device 10 and the universal chuck 30 in accordance with this invention. The precise location and number of grooves 46 may be chosen by the designer to make an appropriate connection between the universal chuck 30 and the permanent chuck of the light emitting device 10.

The external surface of the chuck also comprises a shoulder 42. The shoulder 42 defines a cylindrical land of a convenient size. The land is used to locate a light shield 50 of the type illustrated in FIG. 5.

Figure 5:
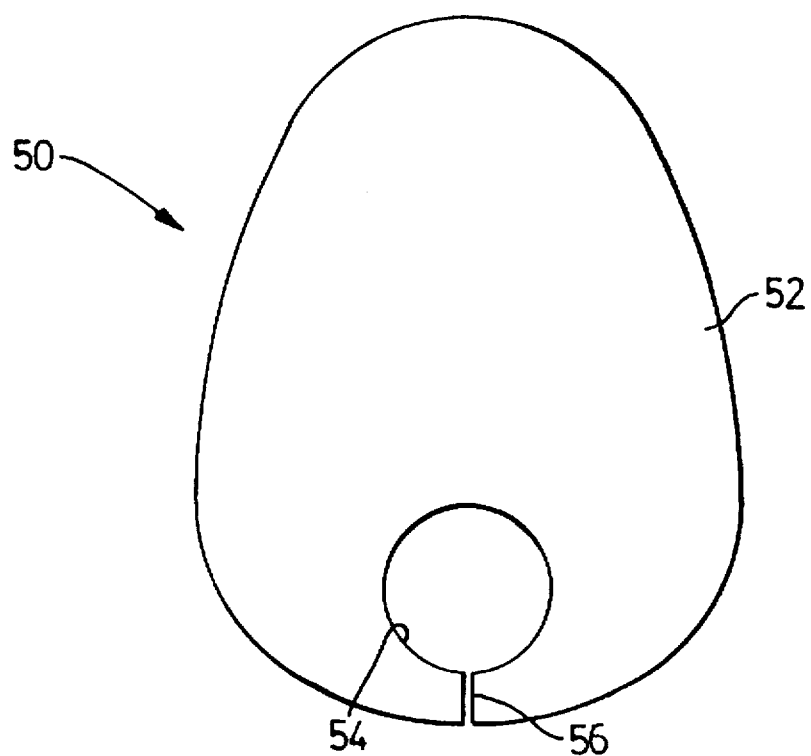
FIG. 5 is a side view of a light shield which may be used with the chuck of FIG. 2.

When the instrument 10 is being used to cure dental resins it is desirable to provide a light shield to protect the eyes of the health care workers using the device, as well as to minimize or eliminate light that may reach the patient's eye. Conveniently the light shield 50 comprises a substantially planar plastic member 52 that may be manufactured from polycarbonate. Typically the light shield 52 is tinted in a convenient colour such as amber. The thickness of the light shield may be of the order of one-eighth of an inch. In order to accommodate the light shield 50, the cylindrical land of the shoulder 42 also has a dimension substantially the same as the thickness of the light shield 50. As shown in FIG. 5, the light shield 50 defines a circular aperture 54 and a slot 56 extending from the aperture 54 to the peripheral edge of the light guide. The slot 56 provides a certain flexibility to the polycarbonate shield 52 so that it may be resiliently slid onto the land 42 and retained on the shoulder 42.

The chuck 30 also includes an grasping portion 44 which may have a textured finish. The grasping portion 44 has an axial length of convenient size, preferably of at least approximately 2 cm. The textured surface of grasping portion 44 which is cylindrical is provided so that the dentist or health care worker using the light emitting device 10 may rotate the chuck 30 by grasping the textured surface. Accordingly, if the bent portion 26 of the light guide 20 is not oriented in the most convenient location for the particular procedure to be conducted, then the universal chuck may be grasped at the grasping portion 44 and rotated about its axis of symmetry. This allows for rotation of the chuck 30 without the need for the health care worker to touch the fibre optic light guide 20 itself.

The universal chuck 30 defines an internal bore 34 extending through the chuck 30. The bore 34 of the universal chuck 30 is sized to releasably receive the substantially cylindrical shank portion 22 of the fibre optic light guide 20 shown in FIG. 4. Conveniently, whatever is the outside diameter of the shank portion 40 of the universal chuck 30 adapted to fit a particular manufacturer's light emitting device 10, the internal bore 34 will be uniform for each member of the set of chucks 30 so as to permit the manufacture of a single fibre optic light guide 20 which is usable in any manufacturers' light emitting apparatus 10. It is important that the bore 34 in the universal chuck 30 be located so as to properly align the fibre optic light guide 20 with the light emitting source. It is also important that the fibre optic light guide be positioned sufficiently accurately that there is no substantial inefficiency in transfer of light from the light emitting device to the fibre optic light guide 20. Thus, the light receiving end 24 of the fibre optic light guide 20 should be positioned by means of the universal chuck 30 in substantially the same location as was the light receiving end of the fibre optic that was originally intended to be used with the light emitting apparatus 10. To help achieve this it is desirable that the universal chuck 30 be provided with a stop 60 adapted to the light receiving end of the bore 34 to axially align the fibre optic light guide. Upon insertion of the fibre optic light guide 20 into the chuck 30, it is pushed into the universal chuck 30 until if contacts the stop 60 so that the position of the light receiving end 24 of the fibre optic light guide 20 is at a designed location.

As it is desired that the fibre optic light guide 20 should be readily removable from the universal chuck for replacement between patient use, the chuck 30 is designed to releasably secure the fibre optic light guide 20 within the bore 34. Various means may be adopted to secure the fibre optic light guide 20 within the bore 34.

A first means of securing the fibre optic light guide 20 within the bore is the provision of a rubber O-ring. The fibre optic light guide may be manufactured with an infernal hemispherical shaped groove extending circumferentially around the surface of the bore. The rubber O-ring may then be inserted within the bore of the universal chuck providing a resilient surface which will contact the outer diameter of the cylindrical portion of the optical light guide.

Typically in glass based fibre optic light guides the tolerances on the external diameter of the light guide are considerably broader than the tolerances that may be achieved in injection molded acrylic light guides. Accordingly, the rubber O-ring should be made sufficiently resilient that it may be compressed by a larger diameter light guide which remains within tolerance while still adequately retaining and supporting a glass fibre optic light guide which is at the small end of the tolerance range.

Acrylic fibre optic light guides of the type shown in FIG. 4 may be made in an injection molding process. The injection molding process is quite accurate and can produce fibre optic light guides within a much narrower tolerance than is typically achievable with glass fibre optic light guides. As indicated above, acrylic fibre optic light guides utilize the fact of air cladding to produce the appropriate internal reflections of light required to function as a light guide. Accordingly, it is desirable to have relatively little surface contact with an acrylic light guide in order to minimize any light leakage which might occur. Therefore when utilizing an acrylic light guide, a rubber O-ring as discussed above may also be used.

Figure 6:
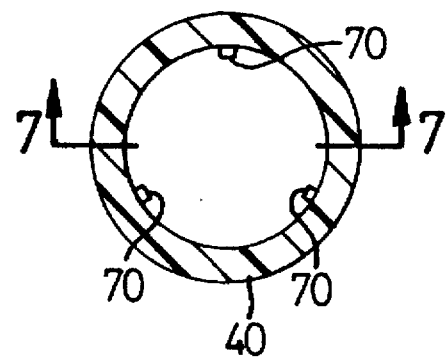
FIG. 6 is a sectional view of a portion of the chuck of FIG. 2.
Figure 7:
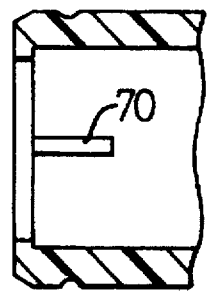
FIG. 7 is a sectional view along the line 7—7 in FIG. 6.
Figure 8:
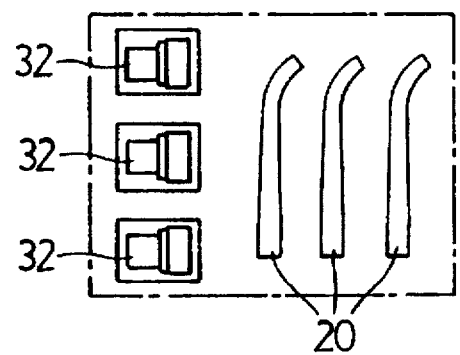

In view of the fact that acrylic light guides may be made with relatively narrow tolerances, an alternate support system is shown in FIG. 6. In FIG. 6 the internal bore 34 of the universal chuck is provided with three ribs 70 extending longitudinally, parallel to the general axis of symmetry of the universal chuck 30. Each rib 70 is a substantially rectangular cross-section with an axial length that may be something less than 2 cm. The ribs 70 are spaced equally about periphery of the bore 34. It has been found that three ribs 70 spaced at 120° about the circumference of the bore 34 will provide sufficient support and retention for the acrylic light guide 20. Each rib 70 may be slightly wedged shape thus projecting inwardly toward the axis of the bore 34 and providing a larger diametrical opening for insertion of the guide and narrowing adjacent stop 60 to grip the acrylic light guide once received within the three support ribs 30. The thickness of the support ribs is kept as small as possible. This provides a releasable support for the light guide 20 wherein the amount of surface area of the acrylic light guide 20 that is gripped by the ribs 70 is relatively minimal and there is not significant impairment of the light transmission properties of the light guide 20 even though the ribs 70 do eliminate the air cladding at the area of contact.

With the universal chuck as described with respect to the preferred embodiment shown in the drawings herein, there is provided a unique system. In accordance with the system, a set of universal chucks may be manufactured. Each one of the set of universal chucks 30 will have the appropriate external diameters and configuration to be inserted within the permanent chuck of a particular manufacturer's light emitting device 10. The set of universal chucks thus fit within respective members of a set of medical devices. Regardless of the configuration and diameter of the shank portion 40 of any member of the set of universal chucks, all of the chucks will have the same internal bore 34. Accordingly, when a particular universal chuck 30 is to be inserted into a particular manufacturer's light emitting device 10, a common fibre optic light guide 20 may be used regardless of the particular manufacturer's device. This provides substantial economies in that the fibre optic light guide 20 of given dimension may be used in any manufacturer's light emitting device. Perhaps more importantly, the ready replaceability helps to promote good disinfection procedures. The elimination of cross contamination is becoming even more important with the spread of H.I.V. Once converted by the installation of the appropriate universal chuck 30, the common light guide would fit all such devices. The set of chucks 30 would comprise 2 or more members each member having external dimensions for use with a corresponding one of a set of 2 or more light emitting devices having different internal configuration in the light guide receiving chuck.

While a particular configuration of light guide has been illustrated in FIG. 4, it will be apparent that any type of light guide having appropriate configuration and properties can be used with the universal chuck 30. The common portion is the cylindrical portion 22 adjacent the light receiving end 24. Accordingly, a dental professional may desire to stock all one type of light guide or stock a plurality of different configuration of light guides to facilitate dental work at different locations in the mouth. When the dental professional wishes to conduct a procedure, the dental professional can select from a supply of unopened, disinfected packages or freshly disinfected guides which have been treated in disinfecting equipment and insert the fibre optic into the universal chuck. After insertion the dental professional need not touch the guide until removal. If the angle of the fibre optic guide needs to be aligned for the particular procedure to be performed, then the universal chuck is grasped at the textured surface of the grasping portion 44 and rotated to the desired position. The procedure is then performed. Following completion of the procedure the light guide may be grasped and removed from the universal chuck by pulling axially away from the O-ring or ribs. The used light guide can then be recycled for disinfecting treatment or disposed of as desired.

One of the principle advantages of this chuck is that the chuck promotes good disinfection procedures. It is increasingly important with the onset of virus' such as H.I.V. that medical professionals disinfect instruments to prevent or at least reduce the chances of cross contamination. In accordance with this system, the professional may have a plurality of probes available for use which helps to encourage good disinfection steps between patients.

Further, in order to assist in good disinfection procedures, the chuck may be made of materials which are suitable for autoclaving such as Nylatron. The chuck may be removed from the gun for autoclaving or liquid emersion or the professional may disinfect the chuck using the same procedures as will be used to disinfect the gun, such as by wiping with a suitable liquid.

The present invention may be embodied in other specific forms without departing from the spirit or essential characteristics thereof. The presently disclosed embodiments are therefore to be considered in all respects as illustrative and not restrictive. The scope of the invention is indicated by the appended claims rather than by the foregoing description and all changes which come within the meaning and range of equivalency of the claims are therefore intended to be embraced therein.

I claim:

1. A set of 2 or more universal chucks for use with a set of 2 or more medical devices having a light emitting device and a fibre optic light guide, each member of said set of medical devices having a different internal configuration for releasably retaining a fibre optic light guide, each member of said set of universal chucks having an outside configuration corresponding to the said internal configuration of a respective one of said set of medical devices, so that said member of said set of universal chuck may be releasably retained within said respective medical device;

all of said set of universal chucks having a common internal configuration adapted to releasably retain a fibre optic light guide so that a common fibre optic light guide may be used in any member of said set of medical devices equipped with a member of said set of universal chucks.

2. An assembly of a plurality of universal chucks each said universal chuck for adapting a selected medical device having a permanently mounted chuck for releasably retaining a fibre optic light guide having a first configuration so that a fibre optic light guide having a second configuration may be used in said medical device, each said universal chuck having an external configuration adapted to be releasably retained within a respective one of said permanently mounted chucks and an internal configuration including a bore and configured to releasably retain said fibre optic light guide of said second configuration and a plurality of interchangeable fibre optic light guides for use in said medical devices, which medical devices have a light emitting device and which are intended for use with a fibre optic light guide, all of said universal chucks having a common internal configuration for releasably retaining a fibre optic light guide of said second configuration to any one of said universal chucks, each said fibre optic light guide having a common external configuration adjacent one end thereof adapted to be releasably retained within said common internal configuration of said universal chucks, each of said universal chucks having an external configuration so that said universal chuck may be releasably retained within the permanently mounted chuck of a selected medical device, the external configuration of each universal chuck of said assembly being different and adapted to be releasably retained within the permanently mounted chuck of a selected medical device so that each of said plurality of fibre optic light guides may be releasably attached to any of said selected medical devices.

3. In the assembly according to claim 2, the universal chucks of claim 2 wherein said internal configuration for releasably retaining said light guide of said second configuration comprises 2 or more ribs extending axially of said bore.

4. The chucks of claim 3 comprising three said ribs equally spaced about the circumference of said bore.

5. The chucks of claim 4 wherein said ribs are tapered to project inwardly toward the axis of said bore with the greatest inward projection being located adjacent the light receiving end of said bore.

6. In the assembly according to claim 2, the universal chucks of claim 2, said chucks further comprising stop means within said bore located adjacent a light receiving end of said bore to axially locate said fibre optic light guide within said bore.

7. In the assembly according to claim 2 the universal chucks of claim 2, said chucks comprising a grasping portion, so that said chucks may be grasped and rotated.

8. The chucks of claim 7, said grasping portion having a textured surface.

9. The chucks of claim 7, said chucks having a shoulder portion, said shoulder portion defining a cylindrical land for supporting a light shield.

10. In the assembly according to claim 2 the universal chucks of claim 2, wherein said chucks are made of a material which is readily disinfectable, said material chosen from the group of stainless steel and Nylatron.

* * * * *